United States Patent [19]
Kim et al.

[11] Patent Number: 6,099,523
[45] Date of Patent: Aug. 8, 2000

[54] COLD PLASMA COAGULATOR

[75] Inventors: Soo-In Kim, Seoul, Rep. of Korea; Vladimir Nikolaevich Lisin, Moscow, Russian Federation; Bekker German, Moscow, Russian Federation; Malivanov Sergei, Moscow, Russian Federation

[73] Assignee: Jump Technologies Limited, Queensway, The Hong Kong Special Administrative Region of the People's Republic of China

[21] Appl. No.: 09/159,995

[22] Filed: Sep. 24, 1998

Related U.S. Application Data

[63] Continuation-in-part of application No. 08/947,133, Oct. 8, 1997, abandoned, which is a continuation of application No. 08/495,228, Jun. 27, 1995, abandoned.

[51] Int. Cl.[7] ................................................. A61B 17/36
[52] U.S. Cl. ................................................. 606/40; 606/49
[58] Field of Search ..................... 606/40–42, 49

[56] References Cited

U.S. PATENT DOCUMENTS

| | | | |
|---|---|---|---|
| 3,434,476 | 3/1969 | Shaw | 128/303.1 |
| 3,903,891 | 9/1975 | Brayshaw | 606/40 |
| 3,938,525 | 2/1976 | Coucher | 128/303.1 |
| 3,991,764 | 11/1976 | Incropera | 128/303.1 |
| 4,040,426 | 8/1977 | Morrison, Jr. | 606/40 |
| 4,429,694 | 2/1984 | McGreevy | 606/40 |
| 4,562,838 | 1/1986 | Walker | 128/303.14 |
| 4,589,411 | 5/1986 | Friedman | 128/303.14 |
| 4,781,175 | 11/1988 | McGreevy | 128/303.17 |
| 4,943,290 | 7/1990 | Rexroth | 606/45 |
| 5,041,110 | 8/1991 | Fleenor | 606/34 |
| 5,207,675 | 5/1993 | Canady | 606/40 |

*Primary Examiner*—Robert L. Nasser
*Attorney, Agent, or Firm*—Jacobson, Price, Holman & Stern, PLLC

[57] ABSTRACT

A cold plasma coagulator clots blood bleeding from tissue during surgical operation in an effective manner, by applying unipolar cold plasma to the blood. The cold plasma coagulator has a high frequency power supply, gas dynamic block and plasmotron. The power supply has a rectifier, capacitor storage and voltage inverter. The said plasmotron is assembled in a hermetically sealed case and in which resonance inductor and dielectric tube are located coaxially. One end of the dielectric tube is connected to the gas dynamic block, another end is positioned to eject plasma through output nozzle. A needle corona electrode is located along the axis of the dielectric electrode. The coils of the resonance inductor has a low voltage and high voltage section, the low voltage section of resonance coils being connected to output of the voltage inverter. One pin of the high voltage section is isolated and another one is connected to the needle corona electrode.

10 Claims, 5 Drawing Sheets

$W_2(L_2, C_2)$

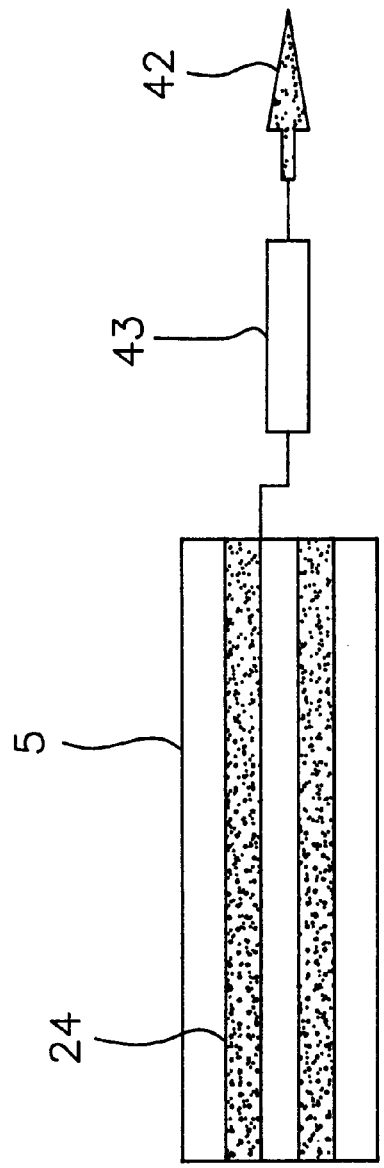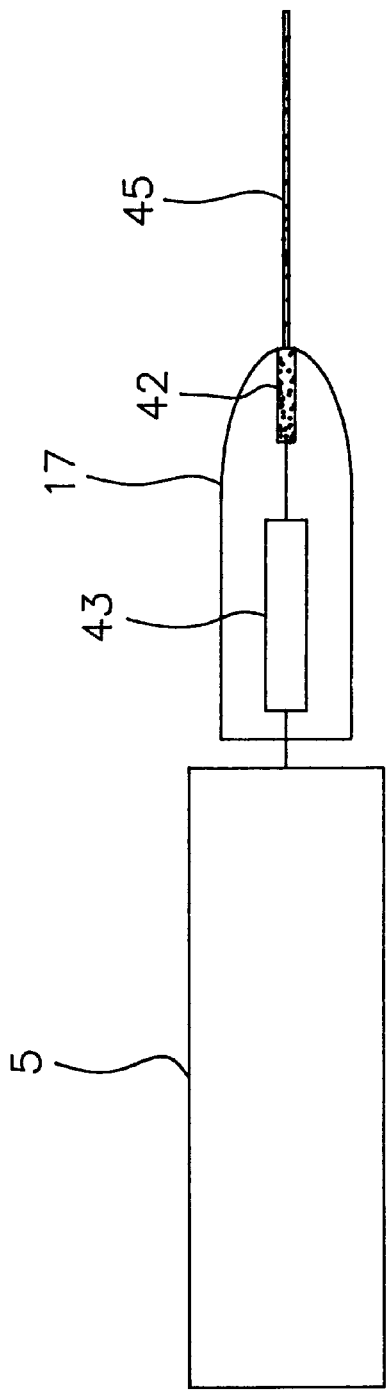

COLD PLASMA COAGULATOR

This is continuation-in-part of U.S. Ser. No. 05/947,133, filed Oct. 8, 1997 now abandoned, which is a continuation of Ser. No. 08/495,228 filed Jun. 27, 1995, now abandoned.

FIELD OF THE INVENTION

The present invention relates to a novel plasma coagulator, more specifically, to a cold plasma coagulator to clot blood bleeding from tissue during surgical operation in an effective and simple manner, by applying unipolar cold plasma.

BACKGROUND OF THE INVENTION

Various types of blood coagulators have been developed in the art to clot the blood, which minimizes the danger resulting from excessive loss of blood during surgical operation. In particular, plasma coagulators which transform inlet gas to plasma and clot the blood by applying the plasma to the tissue during surgical operation, have been widely used in clinical surgery and actively studied by researchers, due to its simple structure and high coagulation efficiency.

For example, U.S. Pat. No. 3,903,891, U.S. Pat. No. 3,938,525, U.S. Pat. No. 3,991,764, U.S. Pat. No. 4,562,838, U.S. Pat. No. 4,781,175 and U.S. Pat. No. 5,207,675 disclose various types of plasma coagulators known in the art.

The plasma coagulators of the prior art are generally classified into two classes, in accordance with their structure, and principle or mode of plasma generation:

One type of plasma coagulators comprise a power supply, gas dynamic path and plasmotron. A cylindrical case of the plasmotron has an output channel for plasma, an anode connected to an electrical circuit of a power supply, and a cathode connected to a cylindrical holder installed coaxially with the case and a rod-like electrode fixed in the end of the holder. The plasma is generated from the plasma forming chamber located between a free end of the electrode and an internal sectional face of the output channel in the form of an arc or glow discharge generated between the anode and the cathode.

The plasma coagulators of the prior art, however, have revealed shortcomings as follows: they essentially require a large cooler and a heat exchanger to cool a heated head of the plasmotron, because the plasma is formed during heating to over several thousand degree of temperature, and the arc generated between the electrodes is very unstable. Further, when the plasma coagulator is practically operated, shunting of the arc arises and the laminar flow of plasma may be disturbed, which finally produces an unstable plasma. When the charge of plasma forming gas is low, unstable plasma is also generated and the plasma discharge can be stabilized only by regulating the charge of gas, which results in malfunction of the plasma coagulator. The limitations of the prior art are presumed to be caused be the fact that the length of the plasma arc is fixed by a variety of parameters dependent on power supply and gas dynamic path, e.g., arc current, charge and pressure of gas, and the diameter of the output channel in the plasma coagulator.

Moreover, the plasma coagulators of the prior art have low coagulation efficiency and increased weight and dimension, and they essentially require an extra ballast resistance in order to regulate the parameters of the power supply and load, and to compensate for the lowering of Volt-Ampere characteristics of the plasma coagulator.

Another type of plasma coagulator comprises a high frequency power supply, gas dynamic path and plasmotron. The plasmotron is assembled in a cylindrical case where a high frequency inductor is positioned, and a dielectric tube functioning as a chamber for plasma generation is located on the axis of coil to help provide the outlet of plasma forming gas. In the plasma coagulator of this type, voltage generated from the high frequency generator which operates at a frequency of tens of MHZ, is transferred to the inductor, and gas flow in the dielectric tube is heated up by the conductive ring current flow, which finally generates the plasma.

The plasma coagulators of the prior art of this type, however, have the disadvantages as follows: the plasma generated from the plasma coagulator are of very high temperature of 4,000 to 9,000° C. and a high frequency current directly conducting to the tissue may be generated from the plasma coagulator, which possibly causes fatal damage to the tissue during surgical operation, and takes a long time to coagulate the blood.

Further, the prior art plasma coagulators, in general, have low coagulation efficiency and it is essential to heat the coil to a high temperature by employing a large capacitor; and, therefore, the mass and dimension of power supply naturally increases to provide the high electric conductivity during gas flow. Especially, when the plasma coagulators of the prior art are applied to the tissue which bleeds in high volume, e.g., to the liver, it is known that the prior art coagulators have very low coagulation efficiency. Moreover, the energy consumption of the coagulators is more than thousands of kV, and an electric shock may be caused when the coagulators are practically used, because the plasma generated therefrom has bipolar characteristics. The prior art plasma coagulators, also, have very complicated structure, which results in increase of the costs for manufacturing. Accordingly, they have been proven to be less satisfactory in the sense that they can not be practically used in clinical surgery.

SUMMARY OF THE INVENTION

A primary object of the invention is, therefore, to provide a cold plasma coagulator to clot the blood bleeding from the tissue during surgical operation which generates unipolar cold plasma to cause no electric shock, reduces the damage of tissue, requires lower energy consumption, and has high coagulation efficiency and simple structure to minimize the mass and dimension.

BRIEF DESCRIPTION OF THE DRAWINGS

The above object of the present invention will become apparent from the following descriptions given in conjunction with the accompanying drawings, in which:

FIGS. 7 and 8 are structural designs of an argon free coagulator in accordance with another embodiment of the invention.

DETAILED DESCRIPTION OF THE INVENTION

Figure 1:
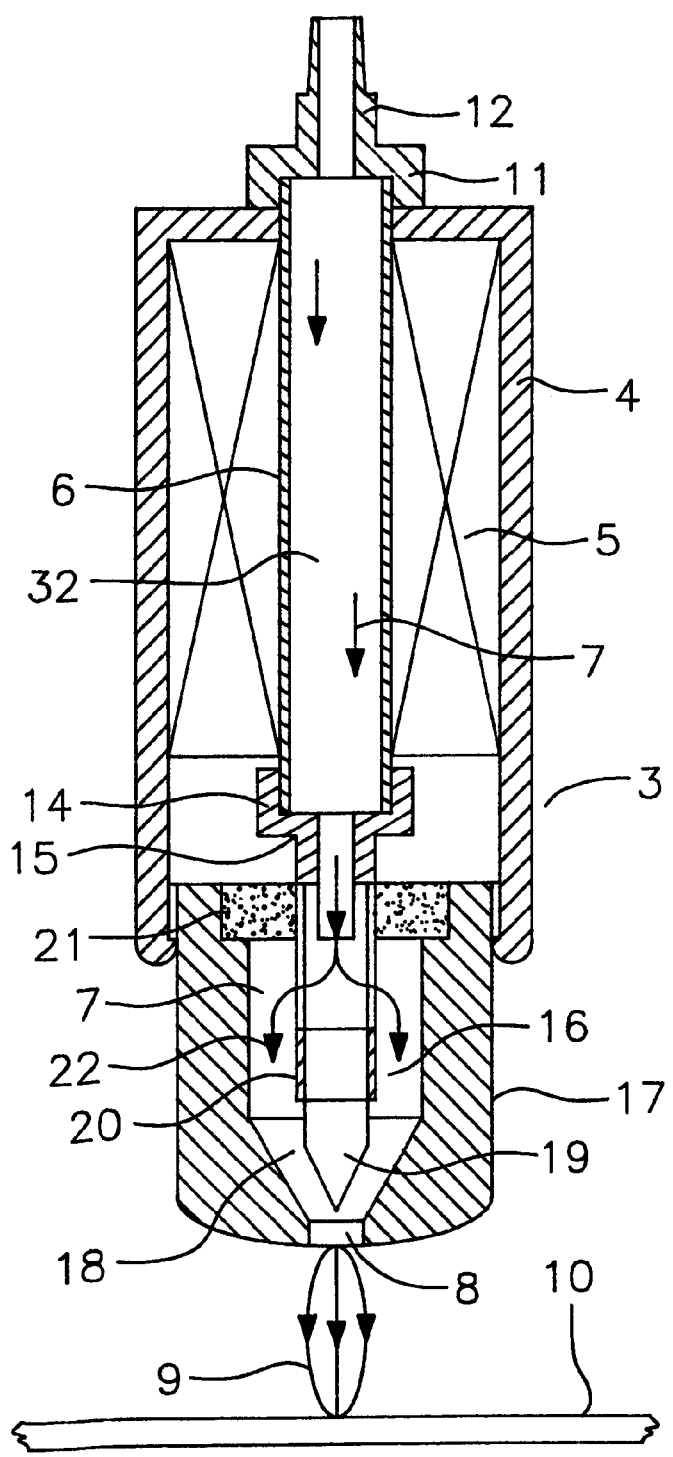
FIG. 1 is a structural diagram of the plasmotron of the cold plasma coagulator.

The cold plasma coagulator of the present invention comprises a high frequency power supply, gas dynamic block and plasmotron. The power supply comprises a rectifier, capacitor storage and voltage inverter. The said plasmotron is assembled in a hermetically sealed case in which a resonance inductor and dielectric tube of cylindrical cartridge are located coaxially. One end of the dielectric tube is connected to the gas dynamic block and the other end is positioned to eject plasma through an output nozzle. Along the axis of the dielectric electrode, a needle corona electrode, is located, coils of the resonance inductor consisting of low voltage and high voltage sections, the low voltage section of resonance coils is connected to an output of the voltage inverter, one pin of the high voltage section being isolated and another one connected to the needle corona electrode.

In this regard, the high voltage section of resonance inductor is provided with cylindrical multi-layer, its non-isolated pin connected to internal layer of the resonance coils and the isolated pin connected to an external layer, and the low voltage section being reeled up atop of the high voltage section in one layer.

Further, employments of a fluoroplastic output nozzle, a sealing nipple installed at one end of the output nozzle to connect with the dielectric tube, a cone-shaped plasma forming chamber provided at another end of the nozzle, facilitate the operation of the plasma coagulator. Preferably, the plasmotron case is constructed in a dismountable banana-shaped form, consisting of two symmetric halves. It is also preferred that the resonance inductor is wound on the fluoroplastic body whose internal and external diameters and height cover the ranges fixed by the following ratio:

$$2 < h/D < 3 \quad 0.3 < d/D < 0.5$$

wherein, D and d represent the external and internal diameters, respectively; and, h represents height of the fluoroplastic body.

The cold plasma coagulator of the invention can generate stable flow of cold plasma even under low charge of plasma forming gas or low current of discharge, which permits decrease of the mass and dimension and efficient operation without applying active capacitor for reactive current.

According to the cold plasma coagulator of the invention, the plasma is excited by the high frequency magnetic field generated from the cavity of resonance coils and by the high frequency induction electrical field from electrode system, and this excitation process does not require additional capacitor for the conductive current.

While the plasma from the prior art coagulator, which is generated by Faraday induction, has bipolar characteristics, the cold plasma from the coagulator of the invention is generated by unipolar induction. Therefore, the currents and potentials for the cold plasma generation obey the law of unipolar induction, and the currents recur to the power supply unit, so the consumption of energy in the plasma coagulator decreases. That is, the plasma coagulator of the invention which generates cold plasma always operates in a form of unipolar induction, so plasma energy can reach to the object through conductive medium. The cold plasma, generated from the plasma coagulator can be activated and accumulated by inductance coils during multi-dimensional parametric resonance process.

A preferred embodiment of the present invention is explained in detail with references on the accompanying drawings, which should not be taken to limit the scope of the present invention.

Figure 2:
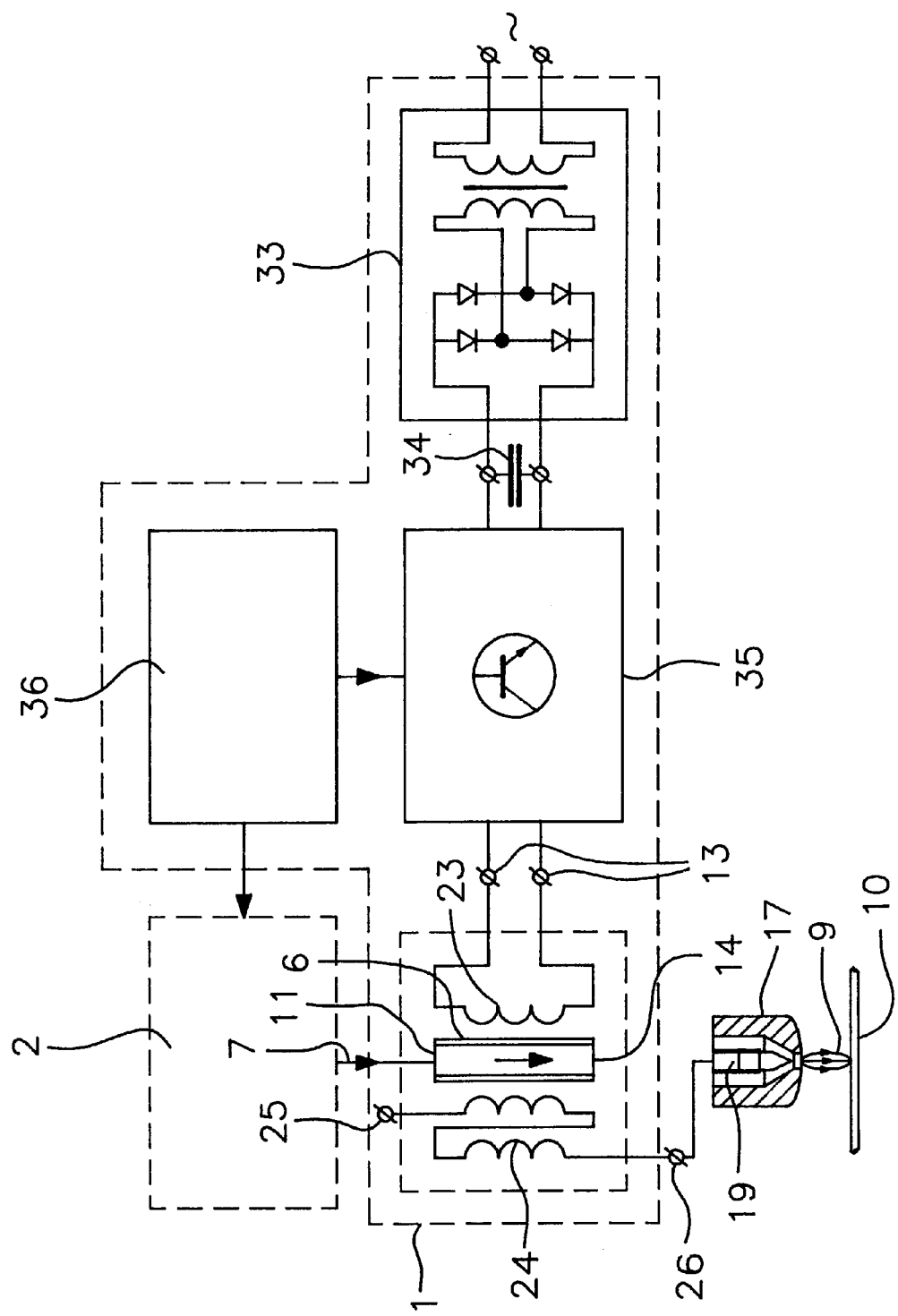
FIG. 2 is an unit-block diagram of the cold plasma coagulator.
Figure 3:
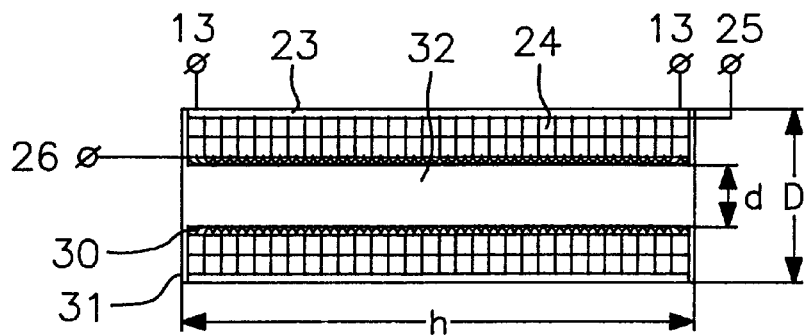
FIG. 3 is a cross-sectional view of the resonance inductor of the cold plasma coagulator.

Referring to FIGS. 1, 2, and 3, the plasma coagulator of the invention comprises a high frequency power supply unit(1), gas dynamic block(2) and plasmotron(3), all of which are assembled in a cylindrical case(4) with a resonance inductor(5) and dielectric tube(6) to flow plasma forming gas(7) located coaxially. The power supply unit comprises a rectifier(33), capacitor storage(34) and voltage inverter(35), for exciting the resonance coils located in the plasmotron(3) by generating a sine wave potential of 30 to 60 V, at a frequency of 50 to 150 kHz and with 50 to 100 W of power, and is constructed to allow the ejection of cold unipolar plasma(9) from output nozzle(8), which coagulates the blood bleeding from the tissue(10).

The first end (11) of the dielectric tube(6) is connected to the gas dynamic block(2) through a plug(12) which also functions as a passage for the power supply entrance(13) to supply the resonance coil with power. The second end(14) of the tube(6) is hermetically connected to the cylindrical cavity(16) of plasma forming electrode(17) through a nipple (15) and under the cavity(16)the plasma forming chamber (18) is positioned. Along the axis of the chamber(18) is installed a needle corona electrode(19), the location of which is fixed by the aid of tubular holder(20) and flange (21). The tubular holder(20) is positioned at the side of radial apertures(22), through which the flow of gas arrives at the plasma forming chamber(18).

The coils of resonance inductor include a low voltage section(23) and high voltage section(24), as depicted in FIG. 2, one pin(25) of the high voltage section(24) is isolated and the other (26) is connected to the needle corona electrode (19) through the tubular holder(20). In this regard, the high voltage section(24) of resonance coil is provided with cylindrical multi-layers, whose non-isolated pin(26) is connected to the internal layer of the resonance coils and the isolated pin(25) to the external layer, respectively; and, the low voltage section(23) is wound on the high voltage section(24) in one layer of the coils. The resonance coils are assembled on a dielectric fluoroplastic body(30) and isolated from each other by the aid of a thin-layer film isolator(31). The dielectric tube(6) is installed in the cylindrical cavity(16) of the coils.

The power supply unit(1) comprises a low voltage block transformer-rectifier(33), capacitor storage(34) and voltage inverter(35). The voltage inverter(35) generates a sine wave signal of the desired resonance frequency. Control block(36) regulates gas pressure through the gas dynamic block(2) and controls voltage of the inverter(35) and tunes the resonance frequency of the inverter. The inverter(35) transforms DC voltage of 25 to 35 V into the frequency with which monovibrator can work.

The capacity range of the plasmotron(3) of the invention is about 50 to 100 $B_T$, the diameter of the output nozzle(8) is less than about 1 mm, and the flow velocity of argon employed as a plasma forming gas is about 2 to 6 L/min.

Since the coagulation of blood by the cold plasma coagulator of the invention is achieved in a form of corona discharge or high voltage glow discharge, the excitation mechanism, concentration and temperature of the plasma would be varied; however, isolation grounding by a second electrode, and conduction of current through the biological object would not be required, since the generation mechanism follows unipolar induction.

Figure 4:
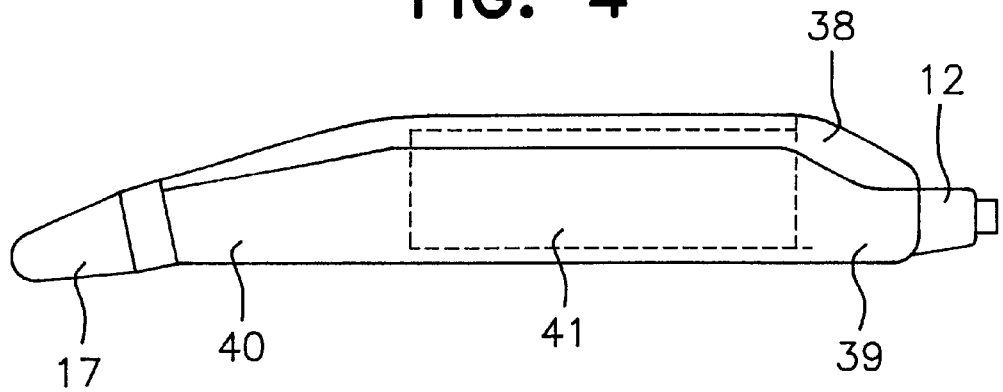
FIG. 4 is a schematic diagram of the plasmotron case of the cold plasma coagulator.

Referring to FIG. 4, the plasmotron case is designed, for convenience during surgical use, as a banana-shaped form assembled from two halves(38),(39). On the narrow part(40) of the case, the dielectric plasma forming electrode(17) is connected, and at the rear side of the case, the plug(12) for conducting and supplying the gas to resonance coils located in cylindrical cavity(41) is positioned. The banana-shaped plasmotron case in an assembled form facilitates convenient use of the plasma coagulator. Further, since the dielectric electrode(17) is also dismountable, the plasma nozzle with various output diameters can be employed in the plasma coagulator of the invention.

The operation mode of the cold plasma coagulator of the invention is described in more detail with references on the accompanying drawings.

Before operating the plasma coagulator, gas dynamic block(2) is connected to the plasma forming gas(helium or argon) which has fixed flow velocity level of 2 to 6 L/min, and the power supply of coagulator is switched on. Gas flow from the block(2), which comprises a cylinder, controller and storage unit, passes through dielectric tube(6) and intersects the central cavity(32) of resonance coils(5), where the magnetic interaction of gas flow and of high frequency magnetic field occurs. Though the ionization of the gas would not be achieved by the magnetic interaction, the gas molecules in the flowing gas are initially activated to increase the plasma generation efficiency of the coagulator.

The gas flow in which reactive magnetic conductivity is increased, arrives at the plasma forming chamber(18) housing the dielectric electrode(17) through nipple(15) and becomes focused at the output nozzle(8) by the dielectric electrode(17) by the formation of a corona discharge on needle electrode(19), which finally results in the generation of cold plasma of about 30° C.

As explained above, because a cold plasma of about 30° C. is generated from the coagulator of the present invention, the damage to the tissue which frequently arises from the coagulators of the prior art, may be minimized.

When the focused flow of cold plasma(9) arrives at the object(10), such as the tissue under surgical operation which functions as a kind of conductive material, coagulation of the blood is carried out. In this regard, plasma forming gas(7) interacts with magnetic field and further interacts with the electric field at the plasma forming chamber(18).

Figure 5:
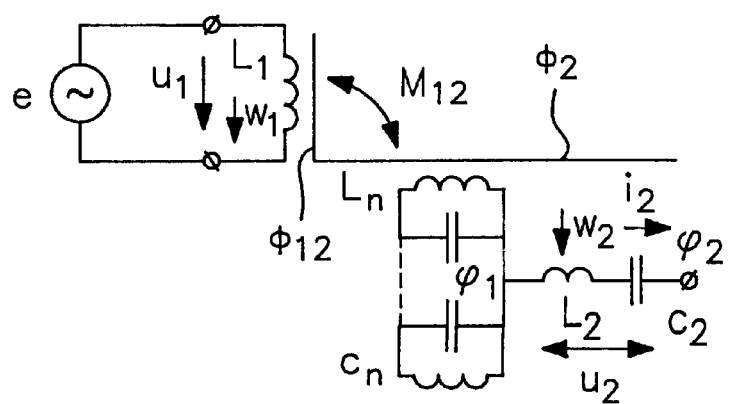
FIG. 5 is an equivalent circuit diagram to resonance characteristics of the cold plasma coagulator; and, FIGS. 6(a) to 6(d) are waveform diagrams for the power supply and resonance circuit of the cold plasma coagulator.

The resonance characteristics of the coils of resonance inductor(5) are shown in FIGS. 3, 4, and 5. In particular, the induction excitation in the low voltage and high voltage sections(23), (24) and the gas flow in central cavity(32) and plasma forming chamber(18) are shown as an equivalent circuit in the diagram of FIG. 5. Referring to FIG. 5 showing the equivalent circuit diagram of resonance induction coils (5), e represents alternating voltage from inverter(35), and $u_1$, $w_1$, and $L_1$ represent voltage, number of turns, and inductance for the coils of low voltage section(23), respectively. In the equivalent circuit diagram, the flow of plasma forming gas is represented as the parallel connection $L_n$-$C_n$: wherein, $L_n$ represents the equivalent inductance of plasma, $C_n$ represents the equivalent capacitance of the plasma and n represents the number of layers of coil.

The mechanism of plasma generation from the coagulator of the invention is defined by the following two emission factors: an emission of charged particles from needle electrode(19) axisymmetrically located in plasma forming chamber(18); and, an emission of the pressurized gas, such as helium or argon, in the chamber(18). The plasma flow(9) possesses low heat capacity due to gas excitation consisting of double stages. In this regard, the plasma forming gas(7) is initially excited by the high frequency magnetic field in the cylindrical cavity(32) at the stage referred to as "parallel parametric resonance". In FIG. 5, the parallel parametric resonance of circuit is shown as an equivalent circuit diagram, including the $L_n$-$C_n$ element.

The gas flow is further excited by the high frequency-reactive electric field in the chamber(18), which is shown in the equivalent circuit diagram of FIG. 5 as $L_2$-$C_2$, being connected in series to form a serial resonant circuit. The high inner resistance of the parallel resonant circuit limits the total arc current of the plasma generated from the output nozzle(8) of the plasmotron. This permits stable plasma injection, lowers the temperature of the plasma being ejected, and improves the blood coagulation efficiency of the plasma.

In addition, the plasma has new properties, that is, it has unipolar characteristics which cause no damage and no electric shock to the tissue; and free reactive current $i_2$(= $i_2'+i_2''$) in the parallel resonance circuit(see: FIG. 6(d)) functions as a carrier of unipolar charges.

In FIG. 5, the high voltage section(24) is depicted as a series resonant circuit of $L_2$-$C_2$ (wherein, the number of turns is represented as $w_2$, the current $i_2$, the voltage $u_2$, and the inductance $L_2$, respectively). The potential for the isolated pin of high voltage section(24) is represented as $\phi_1$, and the potential of the other pin $\phi_2$. $\Phi_1$ and $\Phi_1$ represent the magnetic flows of low voltage and high voltage sections, respectively, and $M_{12}$ represents the mutual inductance for said sections.

Figure 6A:
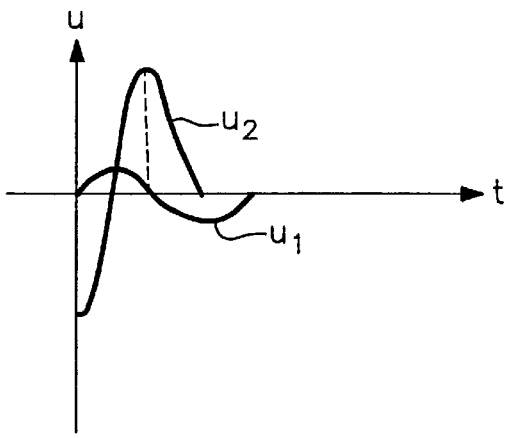

Referring to FIG. 6(a), the main feature of the coagulator under operation is shown as a parametric resonance based on the orthogonal shift of magnetic flows of $\Phi_1$ and $\Phi_2$ (or voltages of $u_1$ and $u_2$ of two coil sections). In the resonance zone, the voltage $u_2$ is n times the transformation factor, which is determined by the equation of Ktr=$w_2/w_1$ at the resonance circuit $L_2$-$C_2$. In this regard, voltage $u_2$ may be represented as the equation(1):

$$u_2 = u_1 \cdot Ktr \cdot n \tag{1}$$

Figure 6B:
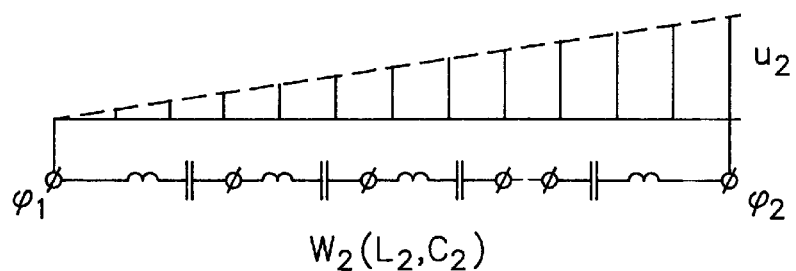
Figure 6C:
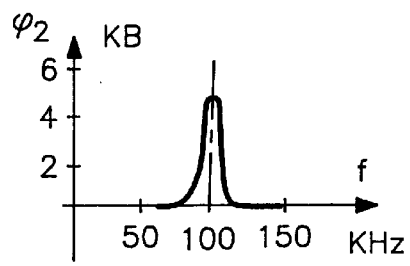
Figure 6D:
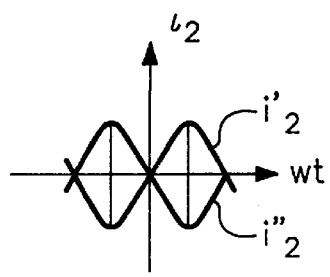

Further, the resonance is accompanied by "polarization" of high voltage section(24), and the field distribution of potential thereby can be depicted as FIG. 6(b). That is, one end of connection is distributed to have a potential of $\phi_1$=0, while another end of connection has a potential of $\phi_2=\phi_{max}$. Especially, the resonant circuit of FIG. 5 resonates at the given frequency of $f_0$=100 kHz as shown in FIG. 6(c). If a parametric connection of resonance circuit exists, it will follow the principle of electromagnetic induction represented as the equations(2) and (3):

$$d(LI)/dt = L \cdot dI/dt + I \cdot dL/dt \tag{2}$$

$$= L \cdot I \tag{3}$$

The pulse voltage $u_2$ of resonance frequency $w_0$ is generated from the circuit of high voltage section(24) of the inductor, and $u_2$ may be represented as the equation(4):

$$u_2 = i_2 \cdot dL/dt \tag{4}$$

The parameters in the circuit of orthogonal flow $\Phi_2$ can be determined by Mateu equations. If $L_{20}$ designates the average value of inductance for high voltage section(24), $L_2(t)$ may be represented as the equations(5) and (6):

$$L_2(t) = L_{20}/(1 - m \cdot \cos 2\omega_0 t) \tag{5}$$

wherein,
  m represents the modulation factor of inductance $L_2$.

$$m = 2/\omega_1 \cdot C_{20} \cdot \rho_n \tag{6}$$

wherein,
  $\omega_1$ represents the frequency of output voltage e;
  $C_{20}$ is the average value of capacitor for high voltage section(24) under parametric resonance state; and,
  $\rho_n$ represents wave resistance of the load(plasma).

The condition of excitation for the parametric resonance may be determined by the equation(7):

$$\omega_0 = \omega_1 \ m > 2Q \ Q = \omega_1 \cdot C_{20} \cdot \rho_n \quad (7)$$

$$\omega_0^2 = 1/L_{20} \cdot C_{20}$$

wherein,

Q is the factor of merit for the resonant circuit.

At this condition, the gas flow(7) interacts with magnetic flow $\Phi_2$ through passing the dielectric tube(6) with a velocity V, and its change per time may be determined as a function of $L_2(t)$ as shown in FIG. 6(d), if the current $i_2$ consists of two counterphase harmonics:

$$\Phi_2 = i_2 \cdot L_2(t) \quad (8)$$

Practically, the high voltage section(24) functions on the active capacitor in the form of idle course (its circuit is disconnected galvanically). In this regard, the pin(25) of the section, possessing the potential of $\phi_1 = 0$, is not grounded.

In the area of central cavity(32), the scalar magnetic field $H_0$ influences on the gas, as parametric induction is manifested with frequency $\omega_0$. Pointing flow on the axis of the resonance coils is defined as:

$$\Pi_H = H_0 \times H \quad (9)$$

wherein,

H represents the vectorial magnetic field created by low voltage section(where, the number of turns is $w_1$); and, $H_0$ represents the scalar magnetic field generated by high voltage section(where, the number of turns is $w_2$).

The electrical portion of Pointing flow arrives into the gas from corona electrode(19) located in plasma forming chamber(18):

$$\hbar_E = E_0 \times E \quad (10)$$

wherein, $E_0$ is the scalar electrical field generated by capacitor $C_2$; and, E is the vectorial electrical field generated by section $w_2$.

Specifically, the scalar field is generated when the potential of non-isolated pin(26) has a value of $\phi_1 = 0$ and the potential of isolated pin(25) has the maximum value of 5 to 10 kV. Owing to the scalar field $E_0$ and $H_0$, the cold unipolar plasma is generated from the coagulator, that is, the characteristics of resonance inductance coils are changed by the scalar field $E_0$ and $H_0$, and the bipolar electromagnetic induction is transformed into Tesla unipolar current. In this regard, the maximum value of factor of merit for the coils under the parametric resonance state, which is the excitation state of scalar field of $E_0$ and $H_0$, may be achieved by constructing the structure of the fluoroplastic body as followings:

$$2 < h/D < 3 \quad 0.3 < d/D < 0.5$$

wherein, D and d represent external and internal diameter, respectively; and, h represents height of the fluoroplastic body.

As far as the resonance circuit gives rise to any leakage, the excitation of plasma may be executed without Joule heat transfer from the electrical circuit to the gas flow. Therefore, the phenomenon of cold plasma ejection can be achieved based on new mechanism of carrying the energy of scalar electrical and magnetic field in a flow of neutral gas such as helium or argon. The contraction and focusing of plasma flow(9) can be achieved by controlling the aperture diameter of output nozzle(8), as well as by controlling the size of chamber(18) and working pressure of the gas.

As shown in FIG. 6(b), the spontaneous polarization of section $w_2$ transfers the characteristics of coaxial quarter wave resonator to the coil shown in FIG. 3 on scalar fields $E_0$ and $H_0$, then considerably increases the factor of merit Q, which already does not depend on the active resistance of winding of the resonance circuit. The process of plasma excitation is initiated by polarized currents of section $w_2$ and is executed on a level of a free reactive capacitor. In this regard, a high potential may be directly formed in the plasmotron by the output for the parametric resonance, and the optimum potential formed at section $w_2$ is 5 to 10 kV.

In contrast to the coagulator of the prior art which requires high level of power in generating conductive currents, the cold plasma coagulator of the present invention substantially minimizes the power consumption, due to the fact that the plasma is activated by reactive currents. Moreover, in contrast to the coagulator of the prior art for which the frequency of tens of MHZ has been required, the optimum frequency for the cold plasma coagulator of the invention is about 100 to 150 kHz, which permits the coagulator to employ the transistor inverter or amplifier with an output voltage of 30 to 60 V as the power supply unit, so that the mass and dimensional parameters of power supply unit would be considerably reduced to provide a portable plasma coagulator and that the plasma coagulator would be manufactured in an economical manner.

As clearly demonstrated and illustrated as above, the cold plasma coagulator of the present invention has high coagulation efficiency and can generate unipolar cold plasma to cause no electric shock and to minimize the damages of tissue during surgical operation, requiring lower energy consumption, and has simple structure to reduce the mass and dimension.

Turning to FIGS. 7–8, an argon-free coagulator is also provided, based on the cold plasma coagulator of FIGS. 1–6. In the argon-free coagulator, the air adjacent to needle electrode (42) is used for plasma forming. No additional means, except for matching element (43) and new condition or resonance inductor (5), are used for plasma initiation. The matching element (43) is preferably a high-voltage capacitor with relatively low capacitance. The new condition for resonance inductor (5) implementation is the following:

$$L = 1/4 * (2k+1)\lambda$$

Where: L=length of wire of high voltage section (24) of resonance inductor (5).

k=integer digit, equal or more than zero.

$\lambda$=wavelength, corresponding to frequency of first sequential resonance of resonance inductor (5).

The plasma streamer (45) is formed on the edge of needle electrode (42) and forms the well visible beam with a length of about 0.5 to 2 cm (up to 1 inch) and a cross section of about 0.5 to 2 mm (up to 0.1 inch), which provides the exact targeting of plasma to treaded tissue area and sequentially reduces the risk of accidental traumatic of adjacent tissue and increases the comfort of surgeon works.

Plasma in the air is formed due to noble gasses included in the air, such as nitrogen, argon, helium and others. The plasma is obtained in steady air located close to the end of the needle electrode 42, as well as air flowing through the gas channel in a dielectric electrode of the CPC. The air flow is optimized to form the direction of plasma beam. When air flow is too small, the plasma is directed to the object, nearest to the end of the needle electrode. However, when the air flow is too high, the plasma may disappear. Preferably, the air flow value is close to the argon flow value as noted above with reference to FIGS. 1–6. The pressure is preferably about one atmosphere with the flow rate at zero. Air temperature is preferably around room temperature. High humidity will result in degradation of plasma beam when air is used as a plasma forming gas.

As used in the present configuration, the capacitor 43 affects the capacitance of coil 24. However, this effect is very minor due to the low value of the capacitance on capacitor 43. The capacitor 43 is preferably a matching element, which is necessary to provide plasma forming from air only. Due to the longitudinal character of the field, which is generated by coil 24, at the end of needle electrode 42, high homogeneous high tense alternating electric field is formed. This field excites the gasses of the air and places them into a medastable state. In this state, the gas molecules are easily ionized and longitudinal electric field separates the positive and negative particles in space. As a result, the lifetime of ions and free electrons substantially extends, the temperature of plasma decreases and plasma exists in normal environmental conditions as well. Due to an alternating character of field, the effect of contraction arises and it results in forming a very thin plasma beam.

Interaction of the resonance circuit in producing the plasma using air only is identical to the method described with reference to FIGS. 1–6 above. Here, however, when the plasma is formed in the air only, the coil 24 is configured to maximize the electric potential at the end of needle electrode 42 and becomes sufficient to excite the noble gasses to a metastable state. The wire, forming an inner wound, provides a quarter-wave resonator when one end of which has zero potential and the other end has high voltage potential to form the plasma.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed is:

1. A cold plasma coagulator comprising:
    a house containing a tube having one end that receives gas;
    an inductor surrounding said tube receiving alternating voltage from a source to produce a magnetic field that interacts with the gas passing through said tube; and
    a needle corona electrode at the other end of said tube receiving alternating voltage to react with the gas exiting from said tube to produce a plasma discharge.

2. A cold plasma coagulator as in claim 1 wherein said housing includes an outlet nozzle adjacent the end of said corona electrode at which the plasma discharge is produced, the plasma discharge exiting the housing through said nozzle.

3. A cold plasma coagulator as in claim 1 wherein said inductor has a low voltage winding having terminals for connection to the voltage source and a high voltage winding, a terminal of the high voltage winding being connected to said corona electrode.

4. A cold plasma coagulator as in claim 3 wherein said high voltage winding has first and second terminals, one of said terminals connected to said coona electrode and the other said terminal being electrically isolated.

5. A cold plasma coagulator as in claim 3 wherein said inductor surrounding said tube comprises a parallel resonant circuit and the combination of the inductor high voltage winding and corona discharge electrode comprises a series resonant circuit.

6. The cold plasma coagulator of claim 5 wherein said inductor is wound on a body of insulating material of dimensions $$2<h/D<3 \ 0.3<d/D<0.5$$

fitting around said tube, wherein:

D and d are the external and internal diameters of said body, respectively, and h is the height of said body.

7. A cold plasma coagulator as in claim 6, wherein said high voltage winding has first and second terminals, one of said terminals connected to said corona electrode and the other said terminal being electrically isolated.

8. The cold plasma coagulator of claim 3 wherein said inductor is wound on a body of insulating material of dimensions $$2<h/D<3 \ 0.3<d/D<0.5$$

fitting around said tube, wherein:

D and d are the external and internal diameters of said body, respectively, and h is the height of said body.

9. A cold plasma coagulator as in claim 5 wherein said high voltage winding has first and second terminals, one of said terminals connected to said corona electrode and the other said terminal being electrically isolated.

10. The cold plasma coagulator of claim 1 wherein said inductor is wound on a body of insulating material of dimensions $$2<h/D<3 \ 0.3<d/D<0.5$$

fitting around said tube, wherein:

D and d are the external and internal diameters of said body, respectively, and h is the height of said body.

* * * * *